(12) United States Patent
Hansen et al.

(10) Patent No.: US 8,956,676 B2
(45) Date of Patent: Feb. 17, 2015

(54) COMPOSITION COMPRISING PROTEIN AND DISPERSE FAT

(75) Inventors: Ole Kaae Hansen, Ega (DK); Tommas Neve, Hadsten (DK)

(73) Assignee: Hamlet Protein A/S, Horsens (DK)

( * ) Notice: Subject to any disclaimer, the term of this patent is extended or adjusted under 35 U.S.C. 154(b) by 739 days.

(21) Appl. No.: 12/735,503

(22) PCT Filed: Jan. 22, 2009

(86) PCT No.: PCT/EP2009/050696
§ 371 (c)(1),
(2), (4) Date: Oct. 12, 2010

(87) PCT Pub. No.: WO2009/092754
PCT Pub. Date: Jul. 30, 2009

(65) Prior Publication Data
US 2011/0034394 A1  Feb. 10, 2011

Related U.S. Application Data

(60) Provisional application No. 61/022,542, filed on Jan. 22, 2008.

(30) Foreign Application Priority Data

Jan. 22, 2008  (DK) .................................. 2008 00079

(51) Int. Cl.
| | | |
|---|---|---|
| A23P 1/00 | (2006.01) | |
| A23D 7/005 | (2006.01) | |
| A23C 11/06 | (2006.01) | |
| A23C 11/10 | (2006.01) | |
| A23J 3/14 | (2006.01) | |
| A23J 3/34 | (2006.01) | |
| A23K 1/16 | (2006.01) | |
| A23L 1/20 | (2006.01) | |
| A23L 1/30 | (2006.01) | |
| A23L 1/305 | (2006.01) | |
| A61K 8/64 | (2006.01) | |
| A61Q 19/10 | (2006.01) | |

(52) U.S. Cl.
CPC ............ *A23D 7/0053* (2013.01); *A23C 11/065* (2013.01); *A23C 11/106* (2013.01); *A23J 3/14* (2013.01); *A23J 3/346* (2013.01); *A23K 1/1631* (2013.01); *A23K 1/164* (2013.01); *A23L 1/2008* (2013.01); *A23L 1/3006* (2013.01); *A23L 1/3016* (2013.01); *A23L 1/305* (2013.01); *A23L 1/3055* (2013.01); *A61K 8/645* (2013.01); *A61Q 19/10* (2013.01); *A23V 2002/00* (2013.01); *A61K 2800/85* (2013.01)
USPC ................ 426/519; 426/21; 426/44; 426/62; 426/520; 426/523; 426/531; 426/656

(58) Field of Classification Search
None
See application file for complete search history.

(56) References Cited

U.S. PATENT DOCUMENTS

| | | | |
|---|---|---|---|
| 3,642,493 A | 2/1972 | Arndt | |
| 3,809,771 A | 5/1974 | Mustakas | |
| 3,901,978 A | 8/1975 | Nelson et al. | |
| 4,039,696 A | 8/1977 | Marquardt et al. | |
| 4,129,664 A | 12/1978 | Kruseman et al. | |
| 4,902,526 A | 2/1990 | Sudo et al. | |
| 6,455,081 B1 * | 9/2002 | Han et al. ...................... | 426/36 |
| 2001/0024666 A1 * | 9/2001 | Waggle et al. ................ | 424/757 |
| 2002/0039619 A1 * | 4/2002 | Monagle ....................... | 426/634 |
| 2005/0008604 A1 * | 1/2005 | Schultz et al. ............... | 424/70.14 |

FOREIGN PATENT DOCUMENTS

| | | |
|---|---|---|
| DE | 106 777 | 9/1973 |
| DE | 3540179 A1 * | 11/1985 |
| EP | 0 384 303 | 8/1990 |
| EP | 0 522 800 | 1/1993 |
| EP | 1 389 429 A1 | 2/2004 |

(Continued)

OTHER PUBLICATIONS

Šližytė et al., Process Biochemistry, 2005, vol. 40, p. 3680-3692.*

(Continued)

*Primary Examiner* — Kade Ariani
(74) *Attorney, Agent, or Firm* — Foley & Lardner LLP

(57) ABSTRACT

The present invention relates to a method for the manufacture of a composition comprising proteins and fats, said method providing a simple and non-expensive way of obtaining fat-containing proteinaceous products of high nutritional value that are easy to handle and at the same time possess high stability towards coalescence and oxidation. More particularly, a method is provided for the manufacture of a composition comprising protein and fat in disperse form, the method comprising the following steps: (i) providing a suspension having a pH value higher than 7.0, said suspension comprising water, proteinaceous material, fat, and optionally alkali; (ii) incubating the suspension from (i) at a temperature in the interval 50-150° C.; (iii) homogenizing the suspension from (ii) to form a dispersion; and (iv), if desired, subjecting the dispersion from (iii) to a subsequent treatment; wherein the proteinaceous material in step (i) comprises vegetable-based proteinaceous material, and/or yeast-based proteinaceous material; wherein the suspension in step (i) comprises at least 5% fat by weight of dry matter. The current invention also relates to the compositions obtained by the method and to compositions obtainable by the method of the invention and, further, to the use of these compositions.

37 Claims, No Drawings

(56) References Cited

FOREIGN PATENT DOCUMENTS

| | | |
|---|---|---|
| EP | 1 292 196 B1 | 8/2007 |
| EP | 1 862 079 A1 | 12/2007 |
| GB | 822614 | 10/1959 |
| GB | 937564 | 9/1963 |
| GB | 1 533 084 | 11/1978 |
| GB | 1 510 773 | 5/1998 |
| JP | 2001/78718 A | 3/2001 |
| SU | 1253572 A1 | 8/1986 |
| WO | WO 99/38393 | 8/1999 |
| WO | WO 99/51106 A1 | 10/1999 |
| WO | WO 01/74175 A1 | 10/2001 |
| WO | WO 2004/009054 A2 | 1/2004 |
| WO | WO 2007/120500 A2 | 10/2007 |
| ZA | 996211 | 9/1999 |

OTHER PUBLICATIONS

Ohta et al., Carcinogenesis, 2000, vol. 21, No. 5, p. 937-941.*
Yamada et al., J. Agric. Food Chem., 2005, vol. 53, p. 3931-3936.*
Pedroche et al., Grasas y Aceites, 2004, vol. 55, p. 354-358.*
Ediriweera et al., Journal of Food Science, 1987, vol. 52, No. 3, p. 685-690.*
Fuchs et al., Journal of Food Science, 2006, vol. 75, p. 27-35.*
Volkert et al., Journal of Food Science, 1979, vol. 44, No. 1, p. 93-96.*
NPL search results, Sep. 18, 2013, 1 page.*
International Search Report issued in application No. PCT/EP2009/050696 on May 28, 2009.
Frankel, "Lipid Oxidation," vol. 10, pp. 100-103, 122-127, 1998.
Gennadios et al., "Edible Coatings and Films based on Proteins," Edible Coatings and Films to Improve Food Quality, Chapter 9, pp. 201-223, 254-259, 1994.
American Oil and Chemist Society, "Physical and Chemical Characteristics of Oils, Fats and Waxes," Official Methods and Recommended Practices of the American Oil Chemists' Society, Table of Contents, pp. i-v, 1997.
Dong et al., "Research Progress and Application of Edible Rapeseed Protein," Journal of Cereals and Oils, vol. 12, pp. 11-13, 2005.
American Oil Chemists' Society, "Physical and Chemical Characteristics of Oils, Fats and Waxes, Section 1," Official Methods and Recommended Practices of the American Oil Chemists' Society, 1996.
Gennadios et al., "Edible Coatings and Films Based on Proteins," Edible Coatings and Films to Improve Food Quality, Krochta et al., eds., pp. 201-223, 1994.
Frankel, "Lipid Oxidation," The Oily Press Lipid Library, vol. 10, pp. 100-103, 122-127, 2004.
Hungarian Search Report issued on Jul. 7, 2011 in Singapore application No. 201005291-8.

* cited by examiner

COMPOSITION COMPRISING PROTEIN AND DISPERSE FAT

This is a national stage of PCT/EP09/050696 filed Jan. 22, 2009 and published in English, which has a priority of Denmark no. PA200800079 filed Jan. 22, 2008, claiming benefit of U.S. Provisional application No. 61/022,542, filed Jan. 22, 2008, Hereby incorporated by reference.

FIELD OF THE INVENTION

The present invention relates to a method for the manufacture of a composition comprising proteins and fats. It also relates to the compositions obtained by the method and to compositions obtainable by the method of the invention and, further, to the use of these compositions.

BACKGROUND OF THE INVENTION

The continued increase in world population has accentuated the demand for ingredients suitable for human food and animal feed. It is well known that carbohydrates, proteins and fats are the main ingredients in any food or feed composition.

Due to the nature of oils and fats they are not easy to handle and incorporate in the formulation during manufacture. Furthermore there may be a stability problem during storage due to coalescence and oxidation. Consequently, there is a demand for fat-containing ingredients that facilitate handling and at the same time possess high stability. Some prior art compositions comprising proteins and oils and fats in disperse form can accomplish this. The main drawbacks of these products are that they are expensive to manufacture and generally have a content of substances that do not add to the nutritional value.

This demonstrates the need for a new type of product that is less expensive to manufacture, which at the same time is nutritionally optimized and has good functional properties and possesses high stability on storage as well as in the final formulation.

The film-forming ability of several proteinaceous substances and their use as edible coatings are known in the art. The film is normally formed by casting or upon solvent evaporation from the surface of a solution. Reference is made to Edible Coatings and Films to Improve Food Quality, Chapter 9, p. 201-223; Technomic Publishing Co. Inc., 1994.

WO 2004/009054 discloses a method for encapsulating an encapsulant comprising admixing an oil component which comprises an encapsulant, with an aqueous component, and a film-forming component to form an emulsion, subjecting the emulsion to homogenization to obtain an oil-in-water emulsion comprising oil droplets wherein the oil droplets comprise the encapsulant and have a diameter of less than about 50 μm, and the film-forming component forms a film around the oil droplets and encapsulates said encapsulant, and applying a protective coating on the film-coated droplets to obtain pellets and to prevent diffusion of said oil component to the surface of the pellets. The protective coating comprises at least one member selected from the group consisting of an aqueous corn protein solution, a denatured whey protein solution, a film-forming starch solution, and an alginate. If the film-forming component is a protein it is preferred that the protein is denatured. WO 2004/009054 does not disclose the possibility of encapsulation of an oil component without the final protective coating.

Another way of increasing the encapsulating potential of proteinaceous substances is to form Maillard reaction products between amino acid groups in the proteins and reducing sugars. WO 2001/074175 discloses a method for encapsulation of oxygen sensitive oils or oils containing oxygen sensitive substances in proteins, which have been reacted with carbohydrates containing reducing sugar groups. An aqueous mixture of a protein, preferably casein, and a carbohydrate, preferably a sugar, is heated to within the range of 60 to 160° C. so that Maillard reaction products are formed in the aqueous mixture. The oil phase, up to 50% by weight is then emulsified with the aqueous phase to form microencapsulated particles. The formation of Maillard reaction products may also be done after emulsification prior to drying. The emulsions can be used as food ingredients, optionally after drying to form powders.

Formation of generally insoluble protein polymers by a catalytic cross-linking reaction can also increase the encapsulating potential of proteinaceous substances. JP 2001078718 discloses a method for the production of an active ingredient useful for food, feed, etc., in which the use of an aldehyde as a cross-linking agent is avoided by carrying out an atomization of a cross-linkable protein, a transglutaminase and the active ingredient. The cross-linkable protein is selected from the group consisting of gelatin, casein, soya bean proteins, corn proteins and collagen and is completely mixed with a transglutaminase derived from a microorganism and an aqueous solution of an active ingredient such as a vitamin, a human food additive or an animal feed additive. An atomization of the resultant mixture is then carried out in an inert gas atmosphere loaded with hydrophobic silica, cornstarch or a hydrophobic cornstarch to produce an active ingredient preparation. Subsequent to the atomization the resultant preparation is preferably further dried until the residual moisture content is below 10% by weight.

The most common way of manufacturing powdered fat compositions is by forming an emulsion that comprises water, the fat, proteinaceous substances and an emulsifier. The powdered composition is obtained by drying the emulsion by a suitable process, e.g. spray drying. GB 822614 discloses a free-flowing fatty powder comprising a dried emulsion of a fat and a partial ester of a glycol with a saturated higher fatty acid encapsulated in a hydrophilic solid or in a mixture of such a solid and a sugar or other carbohydrate. The hydrophilic solid is exemplified by dried fat-free milk, whey and butter milk, sodium caseinate, soya protein derivative, gelatin, hydrolyzed fish protein, egg albumen, dried whole egg or egg yolk, cellulose ethers, pectins, alginates, gum arabic, gum tragacanth. Furthermore, a method for the production of the free-flowing fatty powder is disclosed. The method comprises melting the fat together with said partial ester, and with lecithin, if used, emulsifying the melted mixture in a solution of the encapsulating solids, or a mixture of these solids and sugars or other carbohydrates, and then effecting spray drying.

GB 937564 discloses a powdered fat composition and a method of making a water dispersible, water-stable, powdered fat, said method comprising the steps of blending an edible oil together with a film-forming composition comprising a hydrophilic protein and a quantity of water sufficient to hydrate and disperse said protein but not in excess thereof, agitating the blend thus formed to convert the same into a physically bound dispersion consisting of a continuous encapsulating phase comprised of said film-forming composition, and an internal encapsulated phase comprised of said edible oil, and drying said encapsulating phase. Preferred protein comprises fresh egg whites and reconstituted egg white solids.

One objective of the invention is to provide a simple and inexpensive method for the manufacture of a composition comprising proteins and disperse fats. Another objective is that the products produced by the invented method are easy to handle and at the same time possess high stability towards coalescence and oxidation during storage.

Yet a further objective is that the products at the same time have a high nutritional value.

SUMMARY OF THE INVENTION

One or more of the above-mentioned objectives are addressed by the present invention.

In a first aspect, the current invention relates to a method for the manufacture of a composition comprising protein and fat in disperse form, the method comprising the following steps:
  (i) providing a suspension having a pH value higher than 7.0, said suspension comprising water, proteinaceous material, fat, and optionally alkali;
  (ii) incubating the suspension from (i) at a temperature in the interval 50-150° C.;
  (iii) homogenizing the suspension from (ii) to form a dispersion;
  (iv) and, if desired, subjecting the dispersion from (iii) to a subsequent treatment;
wherein the proteinaceous material in step (i) comprises vegetable-based proteinaceous material, and/or yeast-based proteinaceous material; and wherein the suspension in step (i) comprises at least 5% fat by weight of dry matter.

In a second aspect, the present invention concerns a product obtained or obtainable by a method comprising the following steps:
  (i) providing a suspension having a pH value higher than 7.0, said suspension comprising water, proteinaceous material, fat, and optionally alkali;
  (ii) incubating the suspension from (i) at a temperature in the interval 50-150° C.;
  (iii) homogenizing the suspension from (ii) to form a dispersion;
  (iv) and, if desired, subjecting the dispersion from (iii) to a subsequent treatment;
wherein the proteinaceous material in step (i) comprises vegetable-based proteinaceous material, and/or yeast-based proteinaceous material; and wherein the suspension in step (i) comprises at least 5% fat by weight of dry matter. Optionally, such a product may possess a fat content of ~5-70%, or 10-60% by weight of dry matter, and a protein content of 5-80%, or 15-75% by weight of dry matter.

In a third aspect, the present invention pertains to one or more uses of a product according to the invention, comprising e.g. its use as processed food or feed product for human or animal consumption, a milk replacer, or its use in a cosmetic or a pharmaceutical product.

In a fourth aspect, the present invention concerns different products, such as processed food, feed product for human or animal consumption, a cosmetic product, or a pharmaceutical product comprising from 1 to 99% by weight of a product according to the invention.

In a fifth aspect, the present invention concerns a protein composition, as well as a method for providing such a protein composition, wherein said protein composition comprises from 1 to 99% by weight of a product according to the invention, or from 1 to 99% by weight of a product provided by a method according to the invention, wherein said protein composition comprises 99 to 1% by weight of a protein product comprising another protein, such as fermented soya protein and/or yeast protein, wherein said protein composition has e.g. a protein content of 25-80% by weight of dry matter, and a fat content of 30% or less by weight of dry matter.

Definitions

In the context of the current invention, the following terms are meant to comprise the following, unless defined elsewhere in the description.

The terms "about", "around", "approximately", or "~" are meant to indicate e.g. the measuring uncertainty commonly experienced in the art, which can be in the order of magnitude of e.g. +/−1, 2, 5, 10, 20, or even 50%.

The term "comprising" is to be interpreted as specifying the presence of the stated part(s), step(s), feature(s), composition(s), chemical(s), or components, but does not exclude the presence of one or more additional parts, steps, features, compositions, chemical(s) or components. E.g., a composition comprising a chemical compound may thus comprise additional chemical compounds etc.

Fats:

Comprise esters between fatty acids and glycerol. One molecule of glycerol can be esterified to one, two and tree fatty acid molecules resulting in a monoglyceride, a diglyceride or a triglyceride respectively. Usually fats consist of mainly triglyceride and minor amounts of lecithin, sterols, etc. If the fat is liquid at room temperature it is normally called oil. If the fat is semisolid at room temperature and of exotic origin it is referred to as butter, e.g. shea butter. With respect to oils, fats and related products in this context, reference is made to "Physical and Chemical Characteristics of Oils, Fats and Waxes", AOCS, 1996, as well as "Lipid Glossary 2", F. D. Gunstone, The Oily Press, 2004.

Non-Polar Solvents:

Solvents are classified according to the dielectric constant. A non-polar solvent has a dielectric constant in the interval 1-15, e.g. hexane, petroleum ether, diethyl ether, higher alcohols, etc. Non-polar solvents dissolve non-polar compounds like fats through induced dipole interaction.

Proteinaceous Materials:

Comprise organic compounds made of amino acids arranged in a linear chain and joined together by a bond called a peptide bond. At a chain length of up to approximately 50 amino acids the compound is called a peptide, at higher molecular weight the organic compound is called a polypeptide or a protein.

Enzymes:

Enzyme(s) is a very large class of protein substances that act as catalysts. Commonly, they are divided in six classes, and the main classes falling within the scope of this invention can be transferases that transfer functional groups and the hydrolases that hydrolyze various bonds. Typical examples can comprise: protease(s), peptidase(s), galactosidase(s), amylase(s), glucanase(s), pectinase(s), hemicellulase(s), phytase(s), lipase(s), and phospholipase(s).

Chelators:

Chelators or sequestering agents are natural or synthetic compounds that are able to form a water-soluble complex with a substance. The term sequestering agent is reserved for a chelator yielding soluble metal complexes. Natural chelators include e.g. organic acids such as citric acid; EDTA, and salicylic acid, etc. exemplify the group of synthetic chelators.

Salts:

Salts are ionic compounds composed of cations and anions. Common salt-forming cations include: Sodium, potassium and calcium. Common salt-forming anions are organic or inorganic including: acetate, carbonate(s), phosphate(s), sulphate(s) and chloride.

Suitable salts useful in the context of the present invention can be of edible quality and comprise: sodium carbonate, sodium phosphates, sodium bisulphite and all the rest of the salts bearing E number codes for food additives in the European Union.

Dispersion:

Comprises a mixture of at least two immiscible substances. At least one substance is dispersed in the continuous phase. An emulsion is an example of such a two-phase system. In an O/W-type the oil is the dispersed phase and the water is the continuous phase.

A composition comprising protein and fat in disperse form is another example where the oil and part of the protein is in the disperse phase and water is the continuous phase comprising water soluble, low molecular proteins.

Processed Food Products:

Comprise dairy products, processed meat products, sweets, desserts, ice cream desserts, canned products, freeze dried meals, dressings, soups, convenience food, bread, cakes, etc.

Processed Feed Products:

Comprise ready-to-use feed for animals such as piglets, calves, poultry, furred animals, sheep, cats, dogs, fish and crustaceans etc.

Pharmaceutical Products:

Comprise products, typically in the form of tablets or in granulated form, containing one or more biologically active ingredients intended for curing and/or alleviating the symptoms of a disease or a condition. Pharmaceutical products furthermore comprise pharmaceutically acceptable excipients and/or carriers. The products herein disclosed are very well suited for use as a pharmaceutically acceptable ingredient in a tablet or granulate.

Cosmetic Products:

Comprise products intended for personal hygiene as well as improved appearance such as conditioners and bath preparations.

DETAILED DESCRIPTION OF THE INVENTION

In a first aspect, the present invention relates to a method for the manufacture of a composition comprising protein and fat in disperse form, the method comprising the following steps:
 (i) providing a suspension having a pH value higher than 7.0, said suspension comprising water, proteinaceous material, fat, and optionally alkali;
 (ii) incubating the suspension from (i) at a temperature in the interval 50-150° C.;
 (iii) homogenizing the suspension from (ii) to form a dispersion;
 (iv) and, if desired, subjecting the dispersion from (iii) to a subsequent treatment;
wherein the proteinaceous material in step (i) comprises vegetable-based proteinaceous material, and/or yeast-based proteinaceous material; wherein the suspension in step (i) comprises at least 5% fat by weight of dry matter.

A particular characteristic and/or feature of the products obtained by the method of the invention can be that the fat content is only partly extractable in a non-polar solvent. Thus according to an embodiment of the invention, the fat in said composition comprising protein and fat is only partly extractable in a non-polar solvent. Without wanted to be bound by any theory, it is believed that this may be characteristic for fat droplets that are coated with the proteinaceous material and/or a mixture of carbohydrates and proteinaceous material. This increases the stability and the oxidative resistance of the product. Partly extractable in a non-polar solvent means that less than 100%, such as less than 95%, 90%, 80%, 70% 60%, 50%, 40%, 30%, 20%, or 10% of the fat content relative by weight of the fat of the product can be extracted. In another embodiment of this aspect of the present invention at least 10%, 15%, 20%, 25%, 30%, 35%, 40%, 50%, 60%, 70%, 80%, 90% or more than 90% of the fat content of the product, relative by weight of the fat, is not extractable in a non-polar solvent. According to one embodiment of the invention, said non-polar solvent is selected from the group consisting of: solvent with a dielectric constant in the interval 1-15, hexane, petroleum ether, diethyl ether, and higher alcohol.

The vegetable based proteinaceous material provided in step (i) can be disintegrated material/protein, such as disintegrated by one or more of milling or flaking, etc., and it may be extracted or fermented, e.g. full fat soya meal, protein isolates and fermented, solvent extracted soya meal, etc., and it may further comprise yeast protein. In an embodiment, of the invention, the proteinaceous material originates from yeast. According to another embodiment, the proteinaceous material provided in step (i) comprises only yeast protein, or predominantly yeast protein, such as more than 70, 80, 90, 95, 99% by weight or more. In another embodiment, the proteinaceous material comprises a mixture of material from one or more plants and one or more yeasts. In a further embodiment of the invention, the ratio of proteinaceous material originating from one or more plants to proteinaceous material originating from yeast(s) can be around 1:99; 5:95; 10:90; 20:80; 30:70; 40:60; 50:50; 60:40; 70:30; 80:20; 90:10; 95:5; 99:1 (weight/weight).

According to an embodiment of the invention, the proteinaceous material provided in step (i) comprises vegetable based protein and/or yeast protein. According to another embodiment, the proteinaceous material provided in step (i) is or comprises a vegetable based proteinaceous material, a protein extract, or protein isolate from a proteinaceous vegetable. According to yet another embodiment, the proteinaceous material provided in step (i) is a full fat, disintegrated proteinaceous vegetable, a protein extract or isolate from a proteinaceous vegetable. According to a yet a further embodiment, the vegetable based proteinaceous material has been fermented.

The vegetable based proteinaceous material provided in step (i) may originate for example from one or more of soya, pea, lupine, and any mixture thereof, such as a mixture of soya and pea, a mixture of soya and lupine, a mixture of pea and lupine, or a mixture of soya, pea and lupine. Another suitable vegetable based proteinaceous material may originate from a variety of rapeseed within the *Brassica* family, optionally in combination with any of the aforementioned pulses. Thus, according to an embodiment of the invention, the vegetable based proteinaceous material originates e.g. from soya, pea, lupine, a mixture of soya and pea, a mixture of soya and lupine, a mixture of pea and lupine, or a mixture of soya, pea and lupine. According to another embodiment of the invention, the vegetable based proteinaceous material originates from a variety of rapeseed of the *Brassica* family.

According to a further embodiment of the invention, the vegetable based proteinaceous material provided in step (i) the vegetable based proteinaceous material may—apart from proteinaceous material from one or more of soya, pea, lupine, and any mixture thereof, such as a mixture of soya and pea, a mixture of soya and lupine, a mixture of pea and lupine, or a mixture of soya, pea and lupine—further comprise proteinaceous material that originates from a variety of rapeseed of the *Brassica* family. According to a further embodiment of the invention, the ratio of non-rapeseed/non-*Brassica* proteinaceous material to rapeseed/*Brassica* proteinaceous material can be around 1:99; 5:95; 10:90; 20:80; 30:70; 40:60; 50:50; 60:40; 70:30; 80:20; 90:10; 95:5; 99:1 (weight/weight).

According to the invention, it may be required to add fat to provide the suspension in step (i), in order to achieve at least 5% fat by weight. Thus, according to an embodiment of the invention, the fat provided in step (i) is inherent in the proteinaceous material and/or is selected from plant or animal fat(s) and oil(s), including any fraction(s) and any combinations thereof. According to another embodiment of the invention, one or more fat, oil, fat fraction, and/or oil fraction is added to provide the suspension in step (i), wherein said one or more fat, oil, fat fraction, and/or oil fraction is selected from the group consisting of or derived from one or more of e.g. shea fat, sal fat, soybean oil, rapeseed oil, sunflower oil, maize oil, cottonseed oil, olive oil, flax seed oil, rice bran oil, palm oil, coconut oil, palm kernel oil, lecithin, animal fat, fish oil, and any combination(s) thereof.

The water phase in e.g. step (i) can be normal tap water, optionally comprising one or more further compounds and/or additives. In an embodiment of the invention, the water phase may comprise matter and/or dry matter originating from milk, such as whey, permeate and the like. In another embodiment of the invention, the water phase comprises dry or liquid or semi-liquid matter originating from the dairy industry. In a further embodiment of the invention, said matter originating from the dairy industry is a waste product. In yet another embodiment of the invention, the matter originating from milk is selected from the group consisting of one or more of whey, and permeate, and any combination thereof.

According to the invention, one or more additives, such as e.g. enzymes, e.g. proteases, peptidases, etc., and/or chelators, e.g. citric acid, EDTA, etc., and/or salts, e.g. sodium bisulphite, etc., may be present in or added to the water phase, optionally at any step(s). In one embodiment of the invention, one or more enzyme, one or more chelator and/or one or more salt is/are added to the water phase. Suitable enzymes according to the invention comprise e.g. one or more of protease(s), peptidase(s), galactosidase(s), amylase(s), gluconase(s), pectinase(s), hemicellulase(s), phytase(s), lipase(s), and phospholipase(s), and any combination thereof. Thus the enzyme can e.g. be selected from the group consisting of one or more of e.g. protease, peptidase, galactosidase, amylase, gluconase, pectinase, hemicellulase, phytase, lipase, and phospholipase, including any combination thereof. According to another embodiment of the invention, one or more enzyme(s), and/or chelator(s), and/or salt(s) is added to the water phase, such as the water phase provided during step (i).

According to another embodiment of the invention, one or more chelator(s) is added to the water phase, such as the water phase provided during step (i). A suitable chelator can e.g. be one or more chelator(s) selected from the group consisting of one or more of organic acid, citric acid, EDTA, and salicylic acid, including any combination thereof. In another embodiment of the present invention, a natural or synthetic chelator is added. Suitable chelators comprise thus e.g. one or more organic acid(s), citric acid, EDTA, and salicylic acid, and any combination(s) thereof.

Apart from any of the aforementioned enzyme(s) and/or chelator(s), the water phase, such as the water phase provided in step (i) may comprise one or more salts. According to an embodiment of the invention, such one or more salt(s) can selected e.g. from the group consisting of one or more of e.g. sodium salt, potassium salt, calcium salt, acetate, carbonate, phosphate, sulphate, chloride, sodium carbonate, sodium phosphate, sodium bisulphite, and a salt bearing E number codes for food additives in the European Union; including any combinations thereof. In a further embodiment of the invention, a suitable salt is added. In yet another embodiment of the invention, more than one salt, and/or a mixture of two, three, four or more salts selected from e.g. sodium salt(s), potassium salt(s), calcium salt(s), acetate(s), carbonate(s), phosphate(s), sulphate(s), chloride, sodium carbonate(s), sodium bisulphite, a salt bearing an E number code, and any combination thereof. According to the invention, a salt bearing an E number code for food additives in the European Union is suitable.

According to a further embodiment of the invention, no additive is added to the suspension/water phase, such as the water phase provided during step (i). According to yet another embodiment, no enzyme is added to the suspension/water phase, such as the water phase provided during step (i). According to still another embodiment, no chelator is added to the suspension/water phase, such as the water phase provided during step (i). According to yet still another embodiment, no salt is added to the suspension/water phase, such as the water phase provided during step (i).

The suspension in step (i) can be formed by stirring and mixing a vegetable or yeast based proteinaceous material or a mixture of both with a water phase. Commonly, an alkali, e.g. lye of sodium hydroxide, etc., is added to obtain an alkaline pH, i.e. a pH value higher than 7.0, such as a pH in the interval 7.1-11, 7.1-10.0, 7.1-9.0, or 7.1-8.0. Alternatively, a pH around (i.e. a pH of +/−0.1, 0.25, or +/−0.5) 7.5, 8.0, 8.5, 9.0, 9.5, 10.0, 10.5, 11.0 or above 11.5 is obtained. Providing the suspension and obtaining a desired pH is done by the use of standard methods known in the art.

In step (ii), the suspension of step (i) is incubated at a temperature and for a defined period of time. Without wanted to be bound by any theory, it is believed that according to an embodiment of the invention, said period of time is sufficient to e.g. inactivate biologically active material without forming Maillard reaction products that may negatively influence the nutritional, organoleptic or other properties of the final product. Thus according to the invention, the suspension in step (ii) is incubated at a temperature and for a time sufficient to inactivate biological active material without forming Maillard reaction products. According to a further embodiment of the invention, said period of time is between 1 min and 24 hours (h). According to another embodiment, said time period is e.g. around ~5 min, ~10 min, ~15 min, ~20 min, ~25 min, ~30 min, ~35 min, ~40 min, ~45 min, ~50 min, ~60 min, ~1.5 h, ~2 h, ~3 h, ~4 h, ~5 h, ~6 h. According to yet another embodiment, said time period is at the most 2 h, and generally below 2 hours. Common incubation periods may also comprise 1-2 min, 2-5 min, 5-10 min, 10-20 min, 20-30 min, 30-45 min, 45-60 min, 60-90 min, or e.g. 90-120 min. In another embodiment of the invention, the incubation time is more than 2 hours, such as 2-3 h, 3-6 h, 6-9 h, 9-12 h; overnight; 12-18 h, or 18-24 h, or even more than 24 h.

A suitable temperature interval during step (ii) can e.g. be in the interval or between 50-150° C., 60-140° C., 70-130° C., 80-120° C., 90-110° C. or around 100° C. The temperature can also be between 50-60° C., 60-70° C., 70-80° C., 80-90° C., 90-100° C., 100-110° C., 110-120° C., 120-130° C., 130-140° C., 140-150° C. In one embodiment of the invention, the temperature is constant or essentially constant, i.e. +/−0.5, +/−1.0, +/−2.0 or +/−5.0° C. In a further embodiment, the temperature is not constant. In another embodiment of the invention, the suspension is incubated at a temperature in the interval 60-140° C. for a time of less than 120 min.

The incubated suspension may be subjected to homogenization in order to provide dispersion (step iii). This may be performed by the use of standard homogenizing unit operations known in the art, e.g. by high-pressure piston homogenization, ultrasound and high shear rotor-stator mixing, etc.

Fat or a fat containing material may optionally be added to the suspension e.g. before the (final) homogenization in step (iii) to obtain and/or maintain a fat content of at least 5%, 10%, 20%, 25%, 30%, 40%, 50%, 60%, 70% or above 70%, by weight of dry matter. Alternatively, a fat content in the interval 5-10%, 10-20%, 20-50%, 20-30%, 30-40%, 40-50%, 50-60%, 60-70%, or 30-40% by weight of dry matter may be provided. According to an embodiment of the invention, fat or a fat comprising material is added to the suspension in step (i) to obtain a fat content of 5-70%, or 10-60% by weight of dry matter. Suitable fats comprise one or more fat, oil, fat fraction, and/or oil fraction selected or derived from the group of consisting of one or more of e.g. shea fat, sal fat, soybean oil, rapeseed oil, sunflower oil, maize oil, cottonseed oil, olive oil, flax seed oil, rice bran oil, palm oil, coconut oil, palm kernel oil, animal fat, fish oil, and any combination(s) thereof.

Apart from any of the above-mentioned ingredients, one or more edible ingredients such as e.g. emulsifiers, antioxidants, flavors, coloring matter, etc., may optionally be added at any time. Thus, according to the invention, edible ingredients can be added in or during one or more of any one of step(s) (i), (ii), (iii), (iv), or thereafter. In one embodiment of the invention, edible ingredients are added before the final homogenization. According to another embodiment of the invention, one or more edible ingredients are added to the suspension in step (ii), step (iii) and/or step (iv). Suitable edible ingredient may be selected from the group consisting of one or more of emulsifier, antioxidant, flavor, and coloring matter, and any combination thereof.

According to the invention, a product provided in step (iii) can e.g. be subjected to one or more subsequent treatment steps (step (iv)). Such subsequent treatment step(s) may e.g. comprise pH adjustment, and/or reduction of water content. In one embodiment of the invention, the pH of the dispersion may be adjusted to 3.0-7.0, 3.5-5.5, 4.0-5.0 or around 4.5 (i.e. +/−0.25, or +/−0.5) by the addition of an acid of food grade quality. Alternatively, the pH of the product can be adjusted to below 3.0, or 3.0, 3.5, 4.0, 4.5, 5.0, 5.5, 6.0, 6.5, 7.0 or above 7.0. The pH can also be adjusted to around (i.e. +/−0.25 or +/−0.5) 3.0, 3.5, 4.0, 4.5, 5.0, 5.5, 6.0, 6.5, or 7.0. According to an embodiment of the invention, the pH of the dispersion is adjusted to 3.5-5.5 in step (iv).

According to the invention, the dispersion provided in step (iii)—apart from a pH adjustment—may be subjected to one or more subsequent treatment step may consist of a reduction of the water content, such as to a content of not more than 10%, 7.5%, or 5%, or below 5% by weight. In another embodiment spray drying is used to reduce the water content. In a further embodiment the water content is reduced in an atmosphere with reduced oxygen content. The reduction of oxygen to a content lower than that of ambient air can be accomplished by different methods known in the art, such as by blanketing with inert gas, applying superheated steam and the like. According to an embodiment of the invention, the water content of the dispersion is reduced in step (iv). According to a further embodiment, the water content is reduced to a content of not more than 10% by weight. The water content can e.g. be reduced by spray drying. If desired, the water content is reduced in an atmosphere with oxygen content lower than ambient air.

The method according to the invention can e.g. be carried out as a batch process, fed-batch process, and as a semi-continuous or as a continuous process. Individual steps of the invention can also be carried out as a batch process, fed-batch process, and as a semi-continuous or as a continuous process.

According to an embodiment of the invention, one or more step(s), or all steps are carried out as a batch process. According to another embodiment of the invention, one or more step(s), or all steps are as a continuous process. Technical means for performing and controlling said steps are known in the art.

In a second aspect, the present invention also relates to a product obtained by the method of the invention as described above.

In a third aspect, the present invention also relates to a product obtainable by the method of the invention as described above.

Commonly, such a product obtained or obtainable by the method of the invention may possess a fat content of 5-70% by weight of dry matter. The product can also have at least 5%, 10%, 20%, 25%, 30%, 40%, 50%, 60%, 70% or above 70% fat by weight of dry matter. The product can also have around (i.e. +/−0.1, +/−0.5, +/−1.0%) 5%, 10%, 20%, 25%, 30%, 40%, 50%, 60%, 70% or above 70% fat by weight of dry matter. Alternatively, the product has a fat content of 5-70%, 10-60%, 20-50%, or 30-40% by weight of dry matter. According to one embodiment, a product obtained or obtainable by the method of the invention may comprise a fat content of 5-70% by weight of dry matter, or 10-60% by weight of dry matter, and a protein content of 5-80% by weight of dry matter, or 15-75% by weight of dry matter. According to another embodiment of the invention, the fat content is only partly extractable in a non-polar solvent. According to another embodiment, a product obtained by a method according to the invention has a fat content of 5-70%, or 10-60% by weight of dry matter, and a protein content of 5-80%, or 15-75% by weight of dry matter.

Usually, the product according to the invention has a protein content of 5-80% by weight of dry matter. The product can also have at least 5%, 10%, 20%, 25%, 30%, 40%, 50%, 60%, 80% or above 80% protein by weight of dry matter. The product can also have or around (i.e. +/−0.1, +/−0.5, +/−1.0%, +/−2.5 or +/−5%) 5%, 10%, 20%, 25%, 30%, 40%, 50%, 60%, 80% or above 80% protein by weight of dry matter. Alternatively, the product has a protein content of 5-80%, 10-75%; 15-75%, 10-70%, 20-60%, 30-50% or around 40% by weight of dry matter.

The present invention furthermore relates to a product obtained by any method of the invention, wherein the water content is 10% by weight, or higher than 10% by weight. Commonly, such a product is e.g. liquid or paste. Alternatively, when the water content is usually not more than 10% by weight, such as 10% or less than 10%, the product is usually in solid form, such as a powder or a granulate. According to an embodiment of the invention, a product is provided, wherein the product is in the form of a liquid or paste wherein the water content is higher than 10% by weight. According to another embodiment, a product is provided, wherein the product is in solid form and/or wherein the water content is not more than 10% by weight. According to a further embodiment of the invention, a product is provided wherein the fat or fat content is only partly extractable in a non-polar solvent.

According to a further embodiment, a product obtainable by any method, according of the invention is provided. Such a product may have a fat content of 5-70%, or 10-60% by weight of dry matter, a protein content of 5-80%, or 15-75% by weight of dry matter, and from which the fat content is only partly extractable in a non-polar solvent. Optionally, at least 25%, or 50% of the fat relative by weight of the fat of such a product may not be extractable in a non-polar solvent.

The present invention further comprises the use of a product of the invention, for the manufacture of a processed food or feed product for human or animal consumption and in particular such a product where the oxidative stability of the fat is improved compared to that of direct admixed fat to a similar product. The improvement in shelf life is normally predicted by measurement of the life extension in accelerated test. Concerning oxidative stability of lipids reference is made to "Lipid Oxidation", E. N. Frankel, The Oily Press, Vol. 10 1998. The current invention provides also the use of a product according to the invention for the manufacture of a milk replacer. It also comprises the use of a product of the invention for the manufacture of a cosmetic product or a pharmaceutical product.

Thus, an embodiment of the invention concerns the use of a product according to the invention, or a product provided or obtainable by a method according to the invention, for the manufacture of a processed food or feed product for human or animal consumption.

Another embodiment of the invention relates to the use of a product according to the invention, or a product provided or obtainable by a method according to the invention, for the manufacture of a processed food or a feed product. Optionally, said product has an improved oxidative stability of the fat.

A further embodiment of the invention pertains to the use of a product according to the invention, or a product provided or obtainable by a method according to the invention, for the manufacture of a milk replacer.

Yet another embodiment of the invention concerns the use of a product according to the invention, or a product provided or obtainable by a method according to the invention, for the manufacture of a cosmetic product.

Still another embodiment of the invention relates to the use of a product according to the invention, or a product provided or obtainable by a method according to the invention, for the manufacture of a pharmaceutical product.

In a fourth aspect, the current invention may also provide a processed food or feed product for human or animal consumption comprising from 1 to 99% by weight of a product of the invention. In another embodiment of the invention, a cosmetic or pharmaceutical product is provided comprising from 1 to 99% by weight of the product of the invention. Alternatively, the processed food or feed product for human or animal consumption, or the cosmetic or pharmaceutical product comprises more than 1%, 2%, 5%, 10%, 20%, 30%, 40%, 50%, 60%, 70%, 80%, 90%, 95%, or 99% of a product according to the invention. In another embodiment of the invention, the processed food or feed product for human or animal consumption, or the cosmetic or pharmaceutical product comprises around (i.e. +/−0.1, +/−0.5, +/−1.0%, +/−2.5 or +/−5%) 5%, 10%, 20%, 25%, 30%, 40%, 50%, 60%, 70%, 80%, 90% or 95% of a product according to the invention.

According to an embodiment of the invention, a processed food or feed product for human or animal consumption comprising from 1 to 99% by weight of a product according to the invention, or from 1 to 99% by weight of a product provided by a method according to the invention. According to another embodiment of the invention, a cosmetic or pharmaceutical product comprising from 1 to 99% by weight of a product according to the invention, or from 1 to 99% by weight of a product provided by a method according to the invention.

In a fifth aspect, the present invention concerns a protein composition, as well as a method for providing such a protein composition, wherein said protein composition comprises from 1 to 99% by weight of a product according to the invention, or from 1 to 99% by weight of a product provided by a method according to the invention, wherein said protein composition comprises 99 to 1% by weight of a protein product comprising another protein, such as fermented soya protein and/or yeast protein, wherein said protein composition has e.g. a protein content of 25-80% by weight of dry matter, and a fat content of 30% or less by weight of dry matter.

According to an embodiment, a protein composition is provided comprising or containing from 1 to 99% by weight of a product according to the invention, or comprising or consisting from 1 to 99% by weight of a product by a method according to the invention, wherein said protein composition comprises 99 to 1% by weight of a protein product comprising fermented soya and/or yeast protein, wherein said protein composition has a protein content of 25-80% by weight of dry matter, and a fat content of 30% or less by weight of dry matter. Said protein product comprising fermented soya and/or yeast protein can e.g. be a proteinaceous material suitable to be provided in step (i) in e.g. the first aspect of the invention.

Another embodiment concerns a method of providing a protein composition comprising the steps: (i) providing a product provided by a method according to the invention; (ii) providing a protein product comprising fermented soya and/or yeast protein; and (iii) combining 1 to 99% by weight of the product of step (i) with 99 to 1% by weight of the protein product of step (ii). According to a further embodiment of the invention, the product provided in step (iii) has a protein content of 25-80% by weight of dry matter, and a fat content of 30% or less by weight of dry matter. According to an embodiment of the invention, a product provided by said method comprising steps (i), (ii), and (iii) has one or more desirable features.

From tests it is known that a product, such as a protein composition e.g. according to a fifth aspect the invention with a fat content of preferably not more than around 30% by weight has one or more advantageous features, comprising e.g. one or more of: improved storage characteristic(s); improved transportability; significant reduction in compacting e.g. during handling, storage, and/or transport; no compacting during handling, storage and/or transport. Thus, in order to reduce the fat content to around 30% by weight or below, such ~25%, 20%, 15%, 10%, 5%, or in the range of ~5-10%; 10-15%; 15-20%; 20-30%; it can be desirable to dilute the product with e.g. a proteinaceous material, comprising less fat than the protein composition to be diluted. Such proteinaceous material can e.g. be the same, essentially the same or similar to any of the proteinaceous materials disclosed e.g. in the first aspect of the invention, such as a proteinaceous material provided in step (i), comprising e.g. one or more of vegetable based protein; yeast protein; vegetable based proteinaceous material; a protein extract or protein isolate from a proteinaceous vegetable, full fat, disintegrated proteinaceous vegetable; a fermented vegetable-based proteinaceous material; vegetable based proteinaceous material originating e.g. from one or more of soya, pea, lupine, and any mixture thereof, such as a mixture of soya and pea, a mixture of soya and lupine, a mixture of pea and lupine, or a mixture of soya, pea and lupine; vegetable-based proteinaceous material originating from a variety of rapeseed within the *Brassica* family, optionally in combination with any of the aforementioned pulses; vegetable based proteinaceous material comprising—apart from proteinaceous material from one or more of soya, pea, lupine, and any mixture thereof, such as a mixture of soya and pea, a mixture of soya and lupine, a mixture of pea and lupine, or a mixture of soya, pea and lupine—proteinaceous material that originates from a variety of rapeseed of the *Brassica* family; proteinaceous material comprising non-rapeseed/non-*Brassica* proteinaceous material to rapeseed/*Brassica* proteinaceous material in the range of around 1:99; 5:95; 10:90; 20:80; 30:70; 40:60; 50:50; 60:40; 70:30; 80:20; 90:10; 95:5; 99:1 (weight/weight).

According to an sixth aspect of the invention, a related method for the manufacture of a composition comprising protein and fat in disperse form is provided, said method comprising the following steps: (a) providing a suspension by mixing a vegetable or yeast based proteinaceous material or a mixture of both with a water phase containing alkali in an amount sufficient to form a suspension having a pH value higher than 7.0; (b) incubating the suspension from (a) at a temperature in the interval 50-150° C.; (c) if the suspension contains less than 5% fat by weight of dry matter, adding fat or a fat containing material to the incubating suspension in an amount sufficient to obtain a suspension containing at least 5% fat by weight of dry matter; (d) homogenizing the suspension from (b) or (c) to form a dispersion; and (e) if desired, subjecting the dispersion from (d) to a subsequent treatment.

The vegetable based proteinaceous material may be extracted or fermented and may further comprise yeast protein. The vegetable based proteinaceous material may originate from soya, pea, lupine, a mixture of soya and pea, a mixture of soya and lupine, a mixture of pea and lupine, or a mixture of soya, pea and lupine. Another suitable vegetable based proteinaceous material originates from a variety of rapeseed within the *Brassica* family, optionally in combination with any of the aforementioned pulses. The water phase may comprise dry matter from milk, e.g. whey, permeate, etc. Furthermore, the water phase may have added enzymes, e.g. proteases, peptidases, etc., and/or chelators, e.g. citric acid, EDTA, etc., and/or salts, e.g. sodium bisulphite, etc. The suspension in step (b) is incubated at a temperature and for a time sufficient to inactivate biologically active material without forming Maillard reaction products. A suitable temperature is in the interval 60-140° C. for a time of max. 120 min. To the suspension in step (c) is optionally added fat or a fat containing material before the final homogenization to obtain a fat content of 5-70% by weight of dry matter, or 10-60% by weight of dry matter. Further, one or more edible ingredients, such as e.g. emulsifiers, antioxidants, flavors, coloring matter, etc., may optionally be added to the suspension before the final homogenization. As a subsequent treatment in step (e) the pH of the dispersion may be adjusted to 3.5-5.5. In another subsequent treatment step the water content may be reduced, for example to a water content of not more than 10% by weight. In a further embodiment the water content is reduced by spray drying. In yet a further embodiment the water content is reduced in an atmosphere with oxygen content lower than that of ambient air. The method is carried out as a batch process or as a continuous process. In one embodiment the product, obtained by the method of the invention is a liquid or paste wherein the water content is higher than 10% by weight, and in another embodiment the product is in solid form, wherein the water content is not more than 10% by weight, e.g. powder or granulate. In a particular product obtained according to the invention, at least 25% relative by weight of the fat, or at least 50% relative by weight of the fat, is not extractable in a non-polar solvent.

According a seventh aspect of the invention, a product is obtained from a vegetable based proteinaceous material that has been fermented, characterized in that it has one or more of the following features, including any combination(s) and/or permutation(s) thereof: (1) a fat content of 5-70% by weight of dry matter, and a protein content of 25-80% by weight of dry matter; (2) the proteinaceous material comprises vegetable based protein and/or yeast protein; (3) the vegetable based proteinaceous material originates from soya, pea, lupine, a mixture of soya and pea, a mixture of soya and pea, a mixture of soya and lupine, or a mixture of soya, pea and lupine; (4) the water content is not more than 10% by weight; (5) the fat content is only partly extractable in a non-polar solvent; (6) the product is obtained from a vegetable based proteinaceous material comprising fermented soya and yeast, and has a fat content of max. 30% by weight of dry matter, and a protein content of 25-80% by weight of dry matter; optionally the fat content is only partly extractable in a non-polar solvent.

Such a product obtained from a vegetable based proteinaceous material that has been fermented, comprising any one or more of said features (1) to (6) can be used for the manufacture of one or more of: a processed food or feed product for human or animal consumption; a milk replacer; a cosmetic product; a pharmaceutical product. Thus, in an embodiment of the invention, a processed food or feed product for human or animal consumption is provided, containing or comprising from 1 to 99% by weight of a product obtained from a vegetable based proteinaceous material that has been fermented, optionally comprising one or more of said features (1) to (6). In another embodiment of the invention, a cosmetic or pharmaceutical product is provided, containing or comprising from 1 to 99% by weight of a product obtained from a vegetable based proteinaceous material that has been fermented, optionally comprising one or more of said features (1) to (6).

EXAMPLES

Example 1

Method for the Manufacture of a Composition Comprising Full Fat Soya Bean Meal

Whole soya beans were dehulled, flaked and heated in a rotating drum toaster (Dantoaster). After cooling 10 kg of the resulting material was suspended in 113 kg of tap water and disintegrated in a high shear mixer. The pH value of the suspension was adjusted to 8 by the addition of lye of sodium hydroxide. The suspension was heated to 80° C. During the heating the suspension was agitated.

The suspension was further incubated at 140° C., by the injection of live steam under pressure, in a jet cooker (APV). The jet cooking temperature was kept at 140° C. for 30 s in a holding tube. Subsequently, the product was flashed off in a vacuum chamber in which the suspension was cooled to 80° C. After the cooling to 80° C. the suspension was homogenized in a high-pressure piston homogenizer (APV—Rannie Blue Top type 22.51). A pressure of 450 bar was applied in the homogenizer. The homogenized product, a dispersion, had a smooth and homogeneous consistency.

The dispersion was subjected to a subsequent treatment in a pilot plant spray dryer (APV). The resulting product was a free flowing powder with a light brown color.

The dried product had the following composition:

| Component | Content in % by weight |
|---|---|
| Crude protein | 46.6 |
| Crude fat | 24.7 |
| Carbohydrates | 16.8 |
| Crude fiber | 3.5 |
| Ash | 4.9 |
| Water | 3.5 |

The crude fat content was determined according to method B in section 4 of directive 71/393/EOEF.

A Soxhlet extraction according to method A in section 4 of directive 71/393/EOEF of the dried product in diethyl ether revealed that 5.8% by weight of the fat could be extracted. This means that 18.9% by weight of the fat content is not extractable in diethyl ether, which corresponds to that 76.5% relative by weight of the fat content is not extractable in diethyl ether, a non-polar solvent.

A rehydration test was performed on the dried product. Tap water at room temperature was added to the dried product in an amount corresponding to 15% dry matter in the final mixture. After mixing, the product formed a stable and homogeneous dispersion with no fat separation.

A fat extraction test was performed on the dispersion. An amount of 100 ml was extracted in 100 ml of petroleum ether and the mixture was centrifuged.

After centrifugation a three-phase system was seen. On the bottom was a sediment under a yellowish water phase, and on top of the water phase was a colorless partly gelled solvent phase. The solvent phase was collected and it showed a dry matter content of 0.15 g corresponding to 1% of the dry matter content. This indicates that the fat in the dispersion is practically not extractable in petroleum ether, a non-polar solvent.

Example 2

Method for the Manufacture of a Composition Comprising Fermented Defatted Soya Bean Flakes and Vegetable Oils 10 kg of fermented, defatted soya bean flakes (experimental product from Hamlet Protein A/S, DK) was hydrated in 56.6 kg of water and disintegrated in a high shear mixer and heated to 80° C. During the heating time the suspension was agitated. The pH value of the suspension was adjusted to 8.5 by the addition of lye of sodium hydroxide.

The suspension was held at 80° C. and to this was added 178.5 kg of whey permeate with 14% dry matter (Perlac 14 from Arla Foods A/S, DK) preheated to 80° C. The pH value of the mixture was re-adjusted to 8.5 by the addition of lye of sodium hydroxide.

The suspension was further incubated at 80° C. for 10 min.

After the incubation step the suspension was pre-homogenized in a high-pressure piston homogenizer (APV—Rannie Blue Top type 22.51) at 250 bar. After the pre-homogenization step 25 kg fat mixture (80% of palm oil and 20% of coconut oil) was added under stirring. The suspension formed was finally homogenized at 150 bar in the high-pressure piston homogenizer. The resulting dispersion was stable and homogeneous with no sedimentation or fat separation.

The dispersion had the following composition:

| Component | Content in % by weight |
| --- | --- |
| Crude protein | 3.4 |
| Lactose | 10.1 |
| Fat | 13.9 |
| Ash | 0.4 |
| Water | 72.2 |

Example 3

Method for the Manufacture of a Composition Comprising Full Fat Soya Bean Meal and Yeast To 100 g of full fat soya bean meal was added 1.8 g of brewers yeast and the resulting material was suspended in 110 ml of tap water containing 0.1 g Neutrase form Novozymes, DK, and held at 37° C. for 22 hours. Subsequently, the suspension was diluted to a content of 10% dry matter by weight by the addition of water and the pH value of the suspension was adjusted to 8.5 by the addition of lye of sodium hydroxide.

The suspension was further incubated at 80° C. for 15 min.

After the incubation step an aliquot amount of the suspension was homogenized at 80° C. with an IKA-tron T25 laboratory homogenizer at speed 3 (16000 RPM) for one minute. The resulting dispersion was stable and homogeneous and showed no sedimentation or fat separation after one hour.

The invention claimed is:

1. A method for the manufacture of a dispersion composition comprising protein and fat in disperse form, the method comprising:
   (i) providing a suspension having a pH value higher than 7.0, said suspension comprising water, fermented proteinaceous material, one or more fat(s), and optionally an alkali;
   (ii) incubating the suspension from (i) at a temperature in the interval 50-150° C. inclusive; and
   (iii) homogenizing the suspension from (ii) to form a dispersion composition; wherein the fermented proteinaceous material in step (i) comprises fermented disintegrated vegetable-based proteinaceous material and, optionally, yeast-based proteinaceous material, and wherein the suspension in step (i) comprises at least 5% fat by weight of dry matter; and
   the dispersion composition has a fat content of 5-70% by weight of dry matter and a protein content of 5-80% by weight of dry matter, wherein at least 10% of the fat in the dispersion composition of step (iii) cannot be extracted by petroleum ether, and wherein the fat in the dispersion composition exhibits improved oxidative stability as compared to a comparable composition wherein the fat is present as an admixture instead of a dispersion.

2. The method according to claim 1, wherein the fermented disintegrated vegetable-based proteinaceous material is selected from the group consisting of full fat proteinaceous vegetables, protein extracts and isolates from a proteinaceous vegetable.

3. The method according to claim 1, wherein the fermented proteinaceous material in step (i) comprises both fermented disintegrated vegetable-based proteinaceous material and yeast-based proteinaceous material.

4. The method according to claim 1, wherein the vegetable based proteinaceous material originates from soya, pea, lupine, a mixture of soya and pea, a mixture of soya and lupine, a mixture of pea and lupine, or a mixture of pea, soya and lupine.

5. The method according to claim 1, wherein the vegetable based proteinaceous material originates from a variety of rapeseed of the *Brassica* family.

6. The method according to claim 4, wherein the vegetable based proteinaceous material further comprises proteinaceous material that originates from a variety of rapeseed of the *Brassica* family.

7. The method according to claim 1, wherein the one or more fat(s) provided in step (i) is selected from the group consisting of fat present in the fermented proteinaceous material, plant or animal fat(s), and oil(s).

8. The method according to claim 1, wherein the one or more fat(s) provided in step (i) is selected from the group consisting of shea fat, sal fat, soybean oil, rapeseed oil, sunflower oil, maize oil, cottonseed oil, olive oil, flax seed oil, rice bran oil, palm oil, coconut oil, palm kernel oil, lecithin, animal fat, fish oil, and any combination(s) thereof.

9. The method according to claim 1, wherein in the suspension of step (i), the fermented proteinaceous material further comprises dry milk matter.

10. The method according to claim 9, wherein the milk matter is selected from the group consisting of one or more of whey, and permeate.

11. The method according to claim 1, wherein one or more enzyme(s), and/or chelator(s), and/or salt(s) is provided in or added to the suspension of step (i).

12. The method according to claim 11, wherein the enzyme is selected from the group consisting of one or more of protease, peptidase, galactosidase, amylase, gluconase, pectinase, hemicellulase, phytase, lipase, and phospholipase, including any combination thereof.

13. The method according to claim 11, wherein the chelator is selected from the group consisting of one or more of organic acid, citric acid, EDTA, and salicylic acid, including any combination thereof.

14. The method according to claim 11, wherein the salt is selected from the group consisting of one or more of sodium salt, potassium salt, calcium salt, acetate, carbonate, phosphate, sulphate, chloride, sodium carbonate, sodium phosphate, sodium bisulphite, and any combinations thereof.

15. The method according to claim 1, wherein the suspension in step (ii) further comprises a biological active material and is incubated at said temperature interval and for a time sufficient to inactivate the biological active material without forming Maillard reaction products.

16. The method according to claim 15 wherein the suspension is incubated at a temperature in the interval 60-140° C. inclusive for a time of less than 120 min.

17. The method according to claim 1, wherein fat or a fat comprising material is added to the suspension in step (i) to obtain a fat content of 5-70% by weight of dry matter.

18. The method according to claim 1, wherein one or more edible ingredients are added to the suspension in step (ii) or step (iii) and/or to the dispersion after step (iii).

19. The method according to claim 18, wherein the edible ingredient is selected from the group consisting of one or more of emulsifier, antioxidant, flavor, and coloring matter, and any combination thereof.

20. The method according to claim 1, further comprising, after step (iii), adjusting the pH of the dispersion composition to 3.5-5.5.

21. The method according to claim 1, further comprising, after step (iii), reducing the water content of the dispersion composition.

22. The method according to claim 21, wherein the water content is reduced to a content of not more than 10% by weight.

23. The method according to claim 21, wherein the water content is reduced by spray drying.

24. The method according to claim 21, wherein the water content is reduced in an atmosphere with oxygen content lower than ambient air.

25. The method according to claim 1, wherein the method is carried out as a batch process.

26. The method according to claim 1, wherein the method is carried out as a continuous process.

27. A dispersion composition obtained by the method according to claim 1, comprising fermented, vegetable-based proteinaceous material and fat in disperse form, wherein said composition has a fat content of 5-70% by weight of dry matter, and a protein content of 5-80% by weight of dry matter, wherein at least 10% of the fat in the dispersion cannot be extracted by petroleum ether, and wherein the fat in the dispersion composition exhibits improved oxidative stability as compared to a comparable composition comprising an admixture fat instead of a dispersion.

28. The dispersion composition according to claim 27, wherein the composition is in the form of a liquid or paste wherein the water content is higher than 10% by weight.

29. The dispersion composition according to claim 27, wherein the composition is in solid form and/or wherein the water content is 10% or less by weight.

30. A dispersion composition obtained by the method according to claim 1, wherein the dispersion composition has a fat content of 10-60% by weight of dry matter, a protein content of 15-75% by weight of dry matter, wherein at least 25% of the fat content in the dispersion cannot be extracted by petroleum ether, and wherein the fat in the dispersion composition exhibits improved oxidative stability as compared to a comparable composition comprising an admixture fat instead of a dispersion.

31. A processed food or feed product for human or animal consumption comprising the dispersion composition obtained by the method according to claim 1.

32. The processed food or feed product according to claim 31, with improved oxidative stability of the fat.

33. A milk replacer comprising the dispersion composition according to claim 27.

34. A cosmetic product comprising the dispersion composition according to claim 27.

35. A pharmaceutical product comprising the dispersion composition according to claim 27.

36. A processed food or feed product for human or animal consumption comprising from 1 to 99% by weight of the dispersion composition according to claim 27.

37. A cosmetic or pharmaceutical product comprising from 1 to 99% by weight of the dispersion composition according to claim 27.

* * * * *